United States Patent [19]

Chu

[11] Patent Number: 5,041,093

[45] Date of Patent: Aug. 20, 1991

[54] CATHETER WITH FORAMINOUS ANCHOR

[75] Inventor: Michael S. H. Chu, Brookline, Mass.

[73] Assignee: Boston Scientific Corp., Watertown, Mass.

[21] Appl. No.: 473,012

[22] Filed: Jan. 31, 1990

[51] Int. Cl.$^5$ ............................................. A61M 25/00
[52] U.S. Cl. ..................... 604/104; 604/107; 606/198
[58] Field of Search ............... 604/95, 96, 104, 105, 604/107, 280, 266; 606/198

[56] References Cited

U.S. PATENT DOCUMENTS

| | | | |
|---|---|---|---|
| 3,996,938 | 12/1976 | Clark, III | 606/198 |
| 4,154,242 | 5/1979 | Termanini . | |
| 4,571,241 | 2/1986 | Christopher | 604/104 |
| 4,572,186 | 2/1986 | Gould . | |
| 4,650,466 | 3/1987 | Luther | 604/95 |
| 4,758,219 | 7/1988 | Sacks | 604/54 |
| 4,819,751 | 4/1989 | Shimada . | |
| 4,885,003 | 12/1989 | Hillstead | 604/107 |
| 4,921,484 | 5/1990 | Hillstead | 604/104 |

FOREIGN PATENT DOCUMENTS 1234923  2/1967  Fed. Rep. of Germany ...... 606/198

Primary Examiner—Stephen C. Pellegrino
Assistant Examiner—Ralph A. Lewis

[57] ABSTRACT

A catheter to be used for the movement of fluids having means for maintaining the position of that catheter within a preselected location in the body. The device comprises an elongated flexible tubular member with a longitudinally extending lumen through it. An axially and radially elastically extensible, foraminous woven tube having two ends is disposed between the end of the tubular member and a tip, the tip being spaced from the tubular member. The foramina of the woven tube allow the free flow of fluids therethrough. The woven tube is translatable between three configurations: relaxed, extended and over-center. In the relaxed configuration the woven tube has predetermined length and a predetermined diameter, the predetermined diameter which is greater than the outer diameter of the tubular member and preferably an ovoid shape. In the extended configuration the woven tube has a length that is greater than the predetermined length, and further wherein when in the extended configuration, the outer diameter of the woven tube can assume a generally cylindrical shape. In the third configuration, the woven tube assumes an overcenter shape where it is doubled back on itself to form a cup- or disc-like shape.

21 Claims, 3 Drawing Sheets

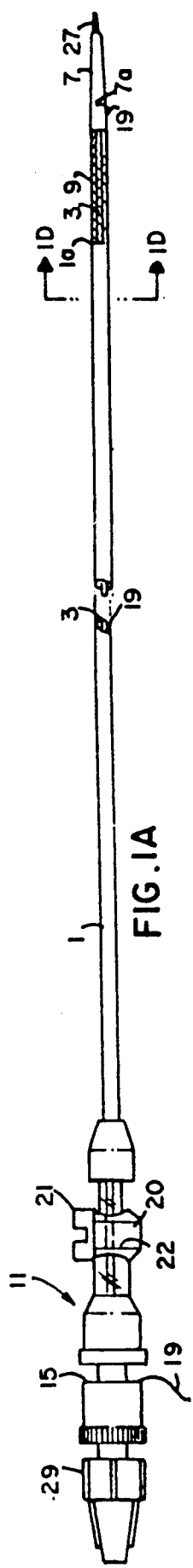
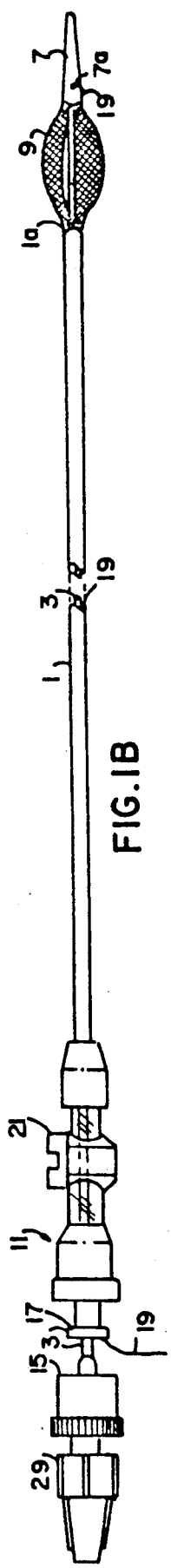
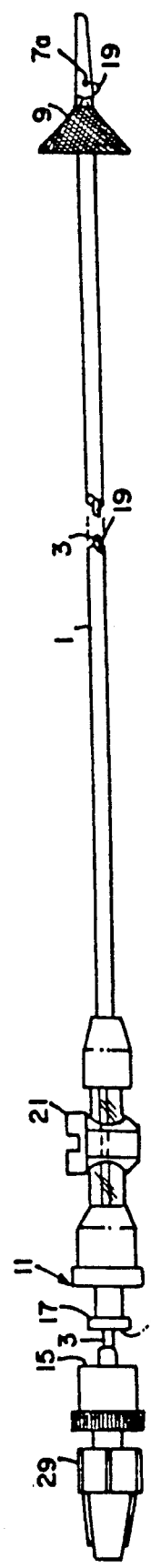
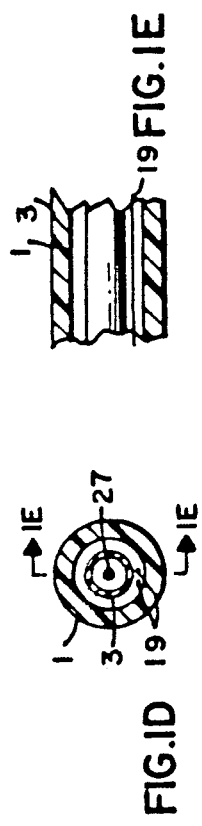
FIG.1A  FIG.1B  FIG.1C  FIG.1D  FIG.1E

CATHETER WITH FORAMINOUS ANCHOR

BACKGROUND OF THE INVENTION

The present invention relates to medical devices and especially to catheters for draining that are to be placed in an organ, duct or vessel of the body for a prolonged period of time. A catheter for draining an organ or vessel can be placed there either subcutaneously (that is by puncturing the skin of the body and directing it through the puncture into the organ) or by inserting the catheter into a natural opening of the body. In many cases, many catheters are removed shortly after they have performed their function and are not kept in place for a long time. On the other hand, some procedures require that the catheters remain in the organ or vessel and with those cases it is necessary to fixedly dispose them so that they will provide for drainage for the desired period. In such cases, the outwardly extending or trailing end of the catheter is usually secured in place by pads and surgical tape. The surgical tape is wrapped around the catheter and attached to the skin to prevent movement or accidental dislodgment therefrom.

According to the present invention, I have discovered that a catheter which is to be disposed in the organ or vessel can be positioned to prevent retrograde movement out of an organ if a multi-shapeable, flexible woven mesh tube formed of plastic strands is disposed between the proximal and distal ends of the catheter. The construction of the woven mesh tube allows it to be translated from a relaxed state in which it has an expanded ovoid configuration to an extended biased configuration in which it has generally cylindrical shape. The extended configuration with the generally cylindrical shape allows the physician to easily place the catheter in the desired location in the organ to be drained. When in place, the woven tube can be allowed to reshape itself to the relaxed state with its ovoid configuration, thereby maintaining the catheter in place. For further security, the woven tube can be translated into a third configuration in which it assumes an over-center shape, that is it can be urged into a disc or cup-like shape. Either of these over-center shapes can maintain the catheter within the organ or vessel to be drained for a prolonged period of time without adversely affecting the drainage of the organ or vessel or the quantity of fluids that are drained. Also these expanded shapes can be readily translated into the extended configuration so that the physician can withdraw the catheter easily.

SUMMARY OF THE PRIOR ART

Catheters that have expandable ends are well known to the art. For example, the U.S. Pat. No. to Termenini, 4,154,242, discloses a catheter that has a self-retainer disposed at the leading end thereof. The retainer includes an array of wings that normally have a cylindrical shape which can be expanded to secure the catheter within an organ to be drained. The wings are formed by a plurality of circumferentially spaced, longitudinally extending slits near the leading end of the catheter. The portions of the tubular member between the slits and intermediate extremities thereof define the wings. When a flexible member disposed in the catheter is retracted, the wings will expand and engage the walls of the organ and retain the catheter in place. I have found, however, that bodily fluids can react with the wings, especially at the ends of the slits, and deteriorate them fairly quickly. When deteriorated, the wings can break off and can become lodged in the organ and damage it. Similarly, the U.S. pat. no. to Sacks et al, 4,758,219, relates to a winged device in which the wings flex outwardly. These wings enclose part of the drainage area because of their shape and location. Moreover, like the wings of Termenini et al, Sacks et al's wings are also susceptible to corrosion from contact with bodily fluids from the organ being drained.

Also, it is known to use a dilator catheter in a procedure known as balloon valvuloplasty to treat calcified, stenotic heart valves. In such procedures, a deflated balloon is inserted through a vein or artery and thence into the heart until the balloon is within the heart valve to be treated. The balloon is then inflated to dilate the diseased valve. After dilatation and completion of the procedure, the balloon is deflated and withdrawn from the cardiovascular system of the patient. Such devices are also shown in the U.S. pat. no. to Shimada et al, 4,819,751, in which a balloon is surrounded with a sheath of woven braid to strengthen it. Patentees, however, are not concerned with the movement of fluids through a catheter and their devices cannot be translated into three configurations.

The U.S. pat. no. to Luther, 4,650,466, discloses an angioplasty device formed of a woven tube disposed at the end of a catheter. The woven tube is supported upon a balloon that is inflated to urge against the inner walls of the vascular system. In the U.S. pat. no. to Gould, 4,572,186, a vessel device is disclosed which uses a braided cylinder of variable radial size. Achieving variations in the radial size is accomplished by varying the axial length of the braided cylindrical member. The braided cylindrical member is disposed upon an elastomeric material that enhances the smoothness of the outer surfaces of the braided cylinder. Axial compression is used to expand the braid but the expansion is accomplished through a seal system and drainage through a tube is not considered.

SUMMARY OF THE INVENTION

The present invention relates to a medical device and more especially to a catheter that is adapted to be operatively associated with the movement of the fluids in an organ or vessel of the body. Especially, the invention concerns the removal of bodily fluids through a catheter comprising an elongated flexible tubular member with an inner lumen terminating in open proximal and distal ends for the passage of fluids therethrough and in which there is a woven tube disposed preferably near the distal end although it may be disposed anywhere between the ends. The woven tube is foraminous and axially and radially elastically extensible. It is normally ovoid in shape and has two open ends. The foramina of the wall of the woven tube allow the free and unobstructed flow of fluids therethrough when the catheter is in place and the woven tube is in either the relaxed or over-center configurations. A cannula may be disposed within the catheter and extends to the tip so as to provide a means to translate the woven tube from its normally ovoid shape to a generally cylindrical shape and vice versa. In addition, the woven tube is translatable into a third configuration in which it is over-center. When the woven tube is translated from its relaxed state to the extended configuration, the outer diameter assumes a generally cylindrical shape. In the third configuration, the woven tube is over-center where it can act as a semi-permanent anchor or catheter location maintenance means. In this over-center configuration, the woven tube assumes a disc-like or cup-like shape and cannot be easily dislodged from the organ or vessel that the catheter is draining.

BRIEF DESCRIPTION OF THE DRAWINGS

FIGS. 1A, 1B and 1C are side views of one embodiment of the catheter of the present invention, each of the three figures showing different configurations for the woven tube. FIGS. 1D and 1E are cross-sectional views taken along the lines 1D—1D and 1E—1E, and showing the interior of the catheter;

DESCRIPTION OF THE PREFERRED EMBODIMENTS

Figure 2A:
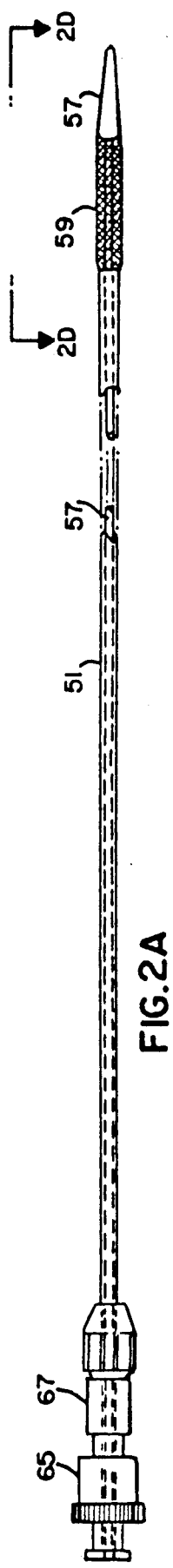
FIGS. 2A, 2B and 2C are side elevational views of another embodiment of the present invention, each of the three figures showing different configurations for the woven tube.

Referring now to FIGS. 1A to 1E, a catheter 1 is shown. A cannula 3 is disposed inside of the catheter 1 to provide stiffening. Cannula 3 is preferably a stainless steel tube that extends through the entire length of the catheter 1 and engages the interior of a tip 7.

The catheter 1 is a tubular member that usually has a length of at least about 20 centimeters and is formed of a material which provides strength and springiness for operation, yet is soft enough to avoid irritation. Materials that have a desired softness and other necessary characteristics include urethanes, silicones and materials sold under the trademark Percuflex (provided by Meditech, Inc. of Watertown, Massachusetts). The selected material must be biocompatible with and inert to bodily fluids, and optimally must have a softness which approaches the softness of body tissue to avoid irritation of the tissue within the organ or vessel being drained during the time the device is in place, which may be for ten days and up to several months.

The center of the catheter 1 bounded by the catheter's walls, that is the inner lumen, extends from a distal end 1a, that is the end that is intended to be placed into the body, to the proximal end, that is the end which extends from the body.

A woven tube 9 such as a expandable braided polyester sleeve manufactured by Schaal Corp., may be disposed adjacent the distal end 1a of the catheter 1. The tube 9 may actually be disposed anywhere between the proximal end and the distal end. The woven tube 9 is preferably thermally bonded around both the outsides of the distal end 1a of the catheter and the tip 7. The woven tube 9 has a radial size that is adjustable by varying the axial length of the tubular member. Variation and axial length is accomplished by moving the tip 7 relative to the distal end 1a of the catheter 1.

The woven tube 9 is formed by thin overlapping strands of flexible polyester material, cross-woven over and under each other in generally clock-wise and counter-clockwise directions. The weave is such that a counter clock-wise strand is able to slidably and intersectingly move with respect to a generally clock-wise strand. Also, the braid is such that foramina are formed at the intersections between clock-wise and counter-clockwise strands so as to allow the passage of fluids. The braided strands are formed of a non-brittle polyester material that can withstand and is resilient in response to the compressive forces that are imparted to the woven tube 9 when it has moved from one configuration to another. To form the woven tube into the ovoid shape, a segment of the generally cylindrical woven tube is compressed by exerting pressure upon opposite ends to cause it to bulge in the middle. When a bulge of the desired diameter is attained, such as shown in FIGS. 1B or 1C, the woven tube, under compression, is heated to set it at that diameter. Generally, the woven tube can be placed in water at about 100° C. for 15 to 30 minutes to set the shape, although exposing it to a stream of hot air at similar temperatures can work also. In the over-center state, the maximum diameter of the woven tube is dependent upon the extended length, diameter and pitch of the woven tube.

Various configurations of the woven tube 9 are shown in FIGS. 1A, 1B and 1C. The normal or relaxed configuration of the woven tube is a generally ovoid shape, as shown in FIG. 1B. In the relaxed configuration, a cannula 3 abuts an axially disposed bore (not shown) disposed within tip 7. Cannula 3 extends through the entire length of catheter 1 and exits through an assembly 11 to terminate in a knob 15, as will be explained later.

In the relaxed configuration shown in FIG. 1B, woven tube 9 has an enlarged central diameter and an ovoid shape, that is it has a predetermined diameter which is larger than the diameter of the catheter 1 and preferably 2 to 3 times larger. Woven tube 9 is translatable to an extended configuration with a generally cylindrical shape, as shown in FIG. 1A. The generally cylindrical shape enables a physician to insert the catheter into the vessel, duct or organ easily. The extended configuration, shown in FIG. 1A, may be accomplished by advancing the cannula 3 distally, and urging locking knob 15 against head 17 and twisting it to engage threads (not shown) disposed inside of locking knob 15.

As shown in FIG. 1A, locking knob 15 has been screwed onto head 17, thereby forcing cannula 3 against the interior of tip 7. As tip 7 is moved relative to distal end 1a, woven tube 9 will stretch to form the generally cylindrical shape. In the generally cylindrical shape, as shown in FIG. 1A, the diameter of the woven tube 9 approximates the diameter of the catheter 1 to enable a physician to insert the device in place for drainage.

Figure 3F:
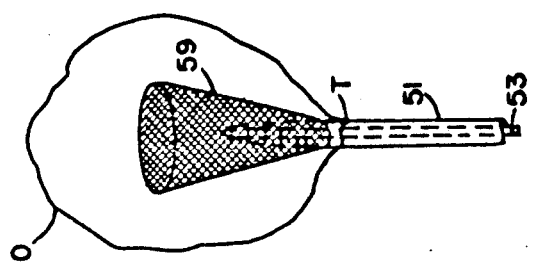
FIGS. 3A to 3C and 3E and 3F are elevational views of the catheter of the present invention disposed in an organ for drainage and particularly showing configurations that the woven tube can assume.
Figure 3E:
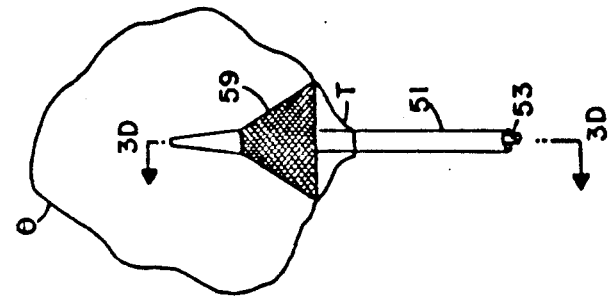
Figure 3D:
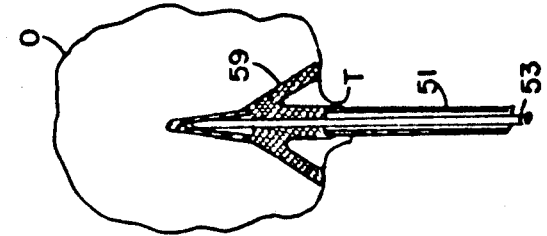
FIG. 3D is a cross sectional view taken along the line 3D—3D of FIG. 3E.
Figure 3C:
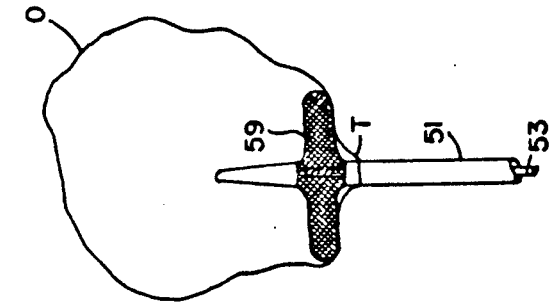

FIG. 1C illustrates a third configuration of the woven tube 9. In the drawing, the woven tube 9 is over-center relative to itself, that is it is doubled back on itself. The over-center configuration of the woven tube 9 is produced by withdrawing the cannula 3 from the catheter 1 and then drawing on a suture 19. Suture 19 is threaded between the outside of cannula 3 and the inside of catheter 1. It is attached to a hole 7a that is disposed in the tip 7. Drawing upon suture 19 pulls tip 7 toward distal end 1a and can cause woven tube 9 to double back on itself, as shown. The over-center configuration is a generally cup-like shape, although disc and tulip-like shapes as shown in FIGS. 3C and 3F, can be formed also, using the same devices to achieve relative movement between tip and the catheter.

A way to lock the tubular member 9 in one position is to use a retention lock 21 on assembly 11 as shown in U.S. Pat. No. 4,643,720. Lock 21 includes a barrel 20 which is disposed inside of a cylinder 22. Barrel 20 is rotatable about an axis within cylinder 22. Movement is accomplished by placing a key 24 in keyway 24a. When rotated 180°, a drill hole 20a in barrel 20 can be aligned with a passageway 23a that is disposed within the outer assembly 11 and is normally arranged to receive the cannula 3. When barrel 20 is turned, suture 19 is entrapped between the walls of cylinder 22 and barrel 20 whereby to hold the woven tube 9 in a fixed position.

A stylet 27 is used in those situations where it is advantageous to insert the catheter 1 by direct percutaneous puncture. The sharp point of the stylet 27 together with the tip 7 is forced through the skin together with the hollow stiffening cannula 3. In this way, the entire assembly of the catheter 1, the cannula 3 and the stylet 27 is introduced percutaneously simultaneously. When the catheter 1 is positioned in an organ, duct or vessel, the stylet 27 and cannula 3 may then be withdrawn. The retention lock 21 may then be twisted to keep sutures 19 in place, after they have been pulled taut to establish the woven tube 9 in its desired configuration.

The catheter 1 may be introduced into the body over a guidewire, not shown, which guidewire replaces the stylet 27. The catheter 51, shown in FIG. 2A, may utilize a guidewire through the cannula 53, the tip 57 being adapted with a narrow bore 58, just wide enough to receive a guidewire, not shown, and not pass the cannula 53 therein.

Figure 2B:
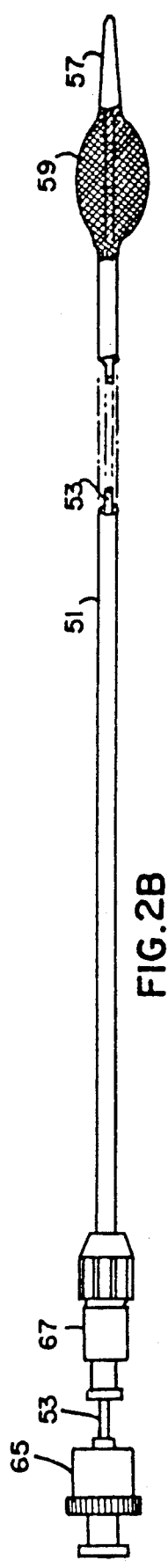
Figure 2C:
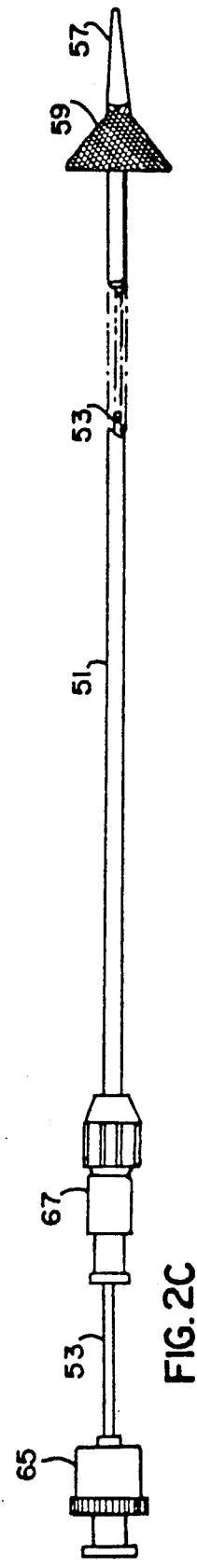
Figure 2D:
FIG. 2D is an enlarged cross-sectional view of the tip of the catheter showing the disposition of a cannula within the tip.

Referring now to FIGS. 2A to 2D, the catheter 51 is shown. Catheter 51 is similar to the catheter shown in FIGS. 1A to 1C, and the woven tube 59 is similar also. The tip 57 is different in that it is adapted to detachably receive a tubular cannula 53. As shown in FIG. 2D, cannula 53, which in this embodiment may be made from a resilient plastic material, snugly engages an axial bore 57a disposed in the interior of tip 57. The bore 57a extends along the tip's length and tapers with decreasing diameter from the tip to the end. In this way, cannula 53 can wedge into the bore 57a and be held there detachably. An enlargement of the tip is shown in FIG. 2D. In this way, cannula 53 can be forced toward the tip 57 so as to shape woven tube 59 into a generally cylindrical shape, as shown in FIG. 2A. The relaxed configuration of woven tube 59 is shown in FIG. 2B, in which knob 65 is disengaged from head 67. As shown in FIG. 2B, cannula 53 is displaced proximally with respect to the catheter 51, leaving woven tube 59 in its relaxed configuration with an ovoid shape. As shown in FIG. 2C, when cannula 53 is displaced even further proximally from catheter 51, woven tube 59 will assume an over-center configuration, such as described with reference to FIG. 1C. Of course, the over-center configuration can be achieved in the embodiment shown in FIGS. 2A to 2C through the use of a taut suture, as discussed previously. In the illustrated embodiment, however, withdrawing the cannula from the catheter can produce the over-center configuration without the sutures. Cannula 53 can also be removed from the inside of tip 57 by a twisting withdrawal motion, so as to leave the woven tube 59 in a desired configuration, and so as to free the entire lumen for the withdrawal of bodily fluids that have to be drained or transported, as may be the case when additional openings (not shown) are disposed through the walls of the catheter 51.

Figure 3B:
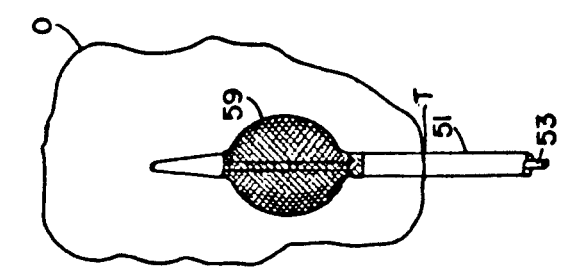
Figure 3A:
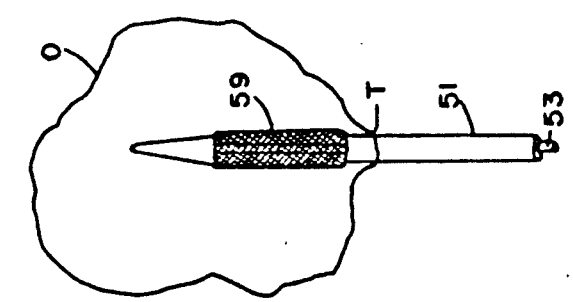

As FIGS. 3A to 3E, various configurations of the woven tube are illustrated (using as examples the FIGS. 2A to 2C embodiments). In FIG. 3A, the catheter 51 is shown entering the organ 0 to be drained or fluid transferred therefrom through a normal bodily opening T. As can be seen, the woven tube 59 is in the extended configuration and has a generally cylindrical shape with a diameter generally conforming to the diameter of the catheter 51. In FIG. 3B, the woven tube 59 is allowed to assume the relaxed configuration with a generally ovoid shape and is shown positioned to allow movement thereof within the organ 0. In FIG. 3C, the woven tube is shown drawn into a disc-like shape and in FIG. 3D and 3E, a cup-like shape is shown. As can be seen especially from FIG. 3D, the woven tube 59 is doubled back on itself when it is in the over-center configuration. This configuration is also useful for the withdrawing of stones from a duct or vessel. The foramina, however, are still open and can pass fluids into the lumen of the catheter 51. In the configuration shown in FIG. 3F, the woven tube 59 is arranged into a tulip-like shape which protectively encloses the tip and which can be used to grasp objects like stones. In each instance, the position of the tube 59 shown in FIGS. 3B, 3C, 3D and 3E us preferably in the middle of the organ "O", and not adjacent the sidewall thereof, to allow patient movement without injuring those walls.

It is apparent that modifications and changes can be made within the spirit and scope of the present invention but it is my intention, however, only to be limited by the scope of the appended claims.

As my invention, I claim.

1. A medical device to be operatively associated with the movement of fluids in a portion of the body, said device comprising:
    an elongated flexible tubular member having a distal and a proximal end and a longitudinally extending lumen therein;
    an axially and radially elastically extensible, normally ovoid in its relaxed configuration, foraminous woven tube having two ends, said woven tube being disposed between the distal end of said tubular member and a tip, said tip being spaced from the distal end of said tubular member, the foramina of said woven tube allowing the free flow of fluids therethrough;
    means disposed in said lumen to effect relative movement between said tubular member and said tim, whereby to translate said woven tube from the normally ovoid shape to a generally cylindrical shape and visa versa.

2. The device according to claim 1 wherein the woven tube is formed of filaments that are braided with strands wound over and under each other in generally clockwise and counterclockwise directions such that the clockwise strands are slidable with respect to the counterclockwise strands and visa versa.

3. The device according to claim 1 wherein the woven tube encircles the tip and the tubular member to connect it thereto.

4. The medical device according to claim 1 wherein the means to effect relative movement is a stylet or cannula disposed through the lumen and the woven tube and into the tip.

5. The medical device according to claim 4 wherein the stylet or cannula is detachably fitted into the tip so that its withdrawal from the tip can cause the woven tube to be changed from the ovoid, relaxed configuration to an over-center configuration.

6. The medical device according to claim 1 wherein the means to effect relative movement is a suture attached to said tip and extending through said woven tube through said lumen to the outside thereof whereby it can be grasped and pulled to change said woven tube from said normally ovoid, relaxed configuration to an over-center configuration.

7. A medical device to be operatively associated with the movement of fluids in a portion of the body, said device comprising:

an elongated flexible tubular member having a distal and a proximal end and a longitudinally extending lumen therein;

an axially and radially elastically extensible, foraminous woven tube having two ends, said woven tube being disposed between the distal end of said tubular member and a tip, said tip being spaced from the distal end of said tubular member, the foramina of said woven tube allowing the free flow of fluids therethrough, said woven tube being translatable between a relaxed configuration and an extended configuration, said woven tube, in the relaxed configuration, having a predetermined length and a predetermined diameter, the predetermined diameter being greater than the outer diameter of said tubular member, said woven tube in the extended configuration having a length that is greater than said predetermined length, and further wherein when in said extended configuration, the outer diameter of said woven tube can assume a generally cylindrical shape, said tip being disposed coaxially with said tubular member, said tip being movable on said axis away from the distal end of said tubular member as said woven tube translates from the relaxed configuration to the extended configuration, the movement being along the mutual axes of said tip and said tubular member;

means disposed within said lumen to effect relative movement between the distal end of said tubular member and said tip, whereby to translate said woven tube from the relaxed configuration to the extended configuration and visa versa and thus change its diameter.

8. The device according to claim 7 wherein the woven tube is formed of filaments that are braided with strands wound over and under each other in generally clockwise and counterclockwise directions such that the clockwise strands are slidable with respect to the counterclockwise strands and visa versa.

9. The device according to claim 7 wherein the woven tube encircles the tip and the tubular member to connect it thereto.

10. The medical device according to claim 7 wherein the means to effect relative movement is a stylet or cannula disposed through the lumen and the woven tube and into the tip.

11. The medical device according to claim 10 wherein the stylet or cannula is detachably fitted into the tip so that withdrawal of the stylet from the tip can cause the woven tube to be changed from the relaxed configuration to an over-center configuration.

12. The medical device according to claim 7 wherein the means to effect relative movement is a suture attached to said tip and extending through said woven tube through said lumen to the proximal end thereof whereby it can be grasped and pulled to change said woven tube from the relaxed configuration to an over-center configuration.

13. A medical device to be operatively associated with the movement of fluids in a portion of the body, said device comprising:

an elongated flexible tubular member having a distal and a proximal end and a longitudinally extending lumen therein;

an axially and radially elastically extensible, foraminous woven tube having two ends, said woven tube being disposed between the distal end of said tubular member and a tip, said tip being spaced from the distal end of said tubular member, the foramina of said woven tube allowing the free flow of fluids therethrough, said woven tube being translatable between a relaxed configuration, an extended configuration and an over-center configuration, said woven tube in the relaxed configuration having a predetermined length and a predetermined diameter, the predetermined diameter being greater than the outer diameter of said tubular member, said woven tube in the extended configuration having a length that is greater than said predetermined length, and further wherein when in said extended configuration, the outer diameter of said woven tube can assume a generally cylindrical shape, said woven tube in the over-center configuration having a cup-like shape in which the walls of the woven tube are doubled over themselves, said tip being disposed coaxially with said tubular member, said tip being movable on said axis away from said tubular member as said woven tube translates between the relaxed configuration, the extended configuration, and the over-center configuration, the movement being along the mutual axes of said tip and said tubular member;

means disposed within said lumen to effect relative movement between the distal end of said tubular member and said tip, whereby to translate said woven tube between the relaxed configuration, the extended configuration and the over-center configuration, and visa versa and thus change its diameter.

means to detachably secure said woven tube in the relaxed configuration and the over-center configuration.

14. A catheter to be operatively associated with a portion of the body, said catheter comprising:

an elongated flexible tubular member having a proximal and a distal end and a longitudinally extending lumen therein;

an axially and radially elastically extensible, foraminous woven tube having two ends, said woven tube being disposed between the distal end of said tubular member and a tip, said tip being spaced from the distal end of said tubular member, the foramina of said woven tube being in fluid flow communication with said lumen whereby to provide an operative association with the body portion, said woven tube being translatable between a relaxed configuration and an extended configuration, said woven tube in the relaxed configuration having a predetermined length and a predetermined diameter, the predetermined diameter being greater than the outer diameter of said tubular member, said woven tube in the extended configuration having a length that is greater than said predetermined length, and further wherein when in said extended configuration, the outer diameter of said woven tube can approximate the outer diameter of said tubular member, said tip being disposed coaxially with said tubular member, said tip being movable on said axis away from said tubular member as said woven tube translates from the relaxed configuration to the extended configuration, the movement being along the mutual axes of said tip and said tubular member;

means disposed within said lumen to effect relative movement between the tubular member and said tip, whereby to translate said woven tube from its extended configuration to its relaxed configuration and thus increase its diameter, thereby to form a means for securing the catheter in place in the body and provide full fluid flow communication between the body and the lumen.

15. A drainage catheter for the transfer of bodily fluids having means for maintaining said catheter within a portion of the body, comprising:

a tubular conduit with a proximal and a distal end and a lumen therein;

a foraminous woven tube disposed in axial alignment with said tubular conduit and in fluid communication with said lumen, the foramina of said woven tube allowing the free flow of fluids therethrough said foraminous tube having an ovoid shape in its relaxed configuration;

means disposed in said lumen to increase the diameter of said woven tube to effectuate disposition and maintenance of said catheter in said portion of the body.

16. A catheter as recited in claim 15, wherein said woven tube is disposed at the distal end of said lumen.

17. A catheter as recited in claim 15 wherein said woven tube is configurable in an over-center configuration.

18. A catheter as recited in claim 17, having means disposed at the proximal end of said tubular conduit for securing said woven tube in its over-center configuration.

19. A catheter as recited in claim 18 wherein said means for securing said woven tube in its over-center configuration comprises a tightenable suture.

20. A catheter as recited in claim 19 wherein said means for securing said woven tube in its extended state comprises a rigid stylet disposed in said conduit.

21. A drainage catheter for the transfer of bodily fluids having means for maintaining said catheter within a portion of the body, comprising:

a tubular conduit with a proximal and a distal end and with a lumen therein;

a foraminous woven tube disposed at the distal end of said tubular conduit in axial alignment with said tubular conduit and in fluid communication with said lumen, the foramina of said woven tube allowing the free flow of fluids therethrough, said foraminous tube having an ovoid configuration in its relaxed configuration, said ovoid configuration having a larger girth than the girth of said conduit;

means disposed in said lumen to increase the diameter of said woven tube to effectuate disposition and maintenance of said catheter in said portion of the body.

* * * * *

UNITED STATES PATENT AND TRADEMARK OFFICE
CERTIFICATE OF CORRECTION

PATENT NO.   : 5,041,093
DATED        : August 20, 1991
INVENTORS    : Chu

It is certified that error appears in the above-identified patent and that said Letters Patent is hereby corrected as shown below:

In column 6, line 44 please delete "tim" and add in its place --tip--.

Signed and Sealed this

Fifteenth Day of February, 2000

Attest:

Q. TODD DICKINSON

Attesting Officer        Commissioner of Patents and Trademarks